United States Patent [19]

Berkowitz

[11] Patent Number: 4,525,673
[45] Date of Patent: Jun. 25, 1985

[54] NMR SPECTROMETER INCORPORATING A RE-ENTRANT FIFO

[75] Inventor: Edward H. Berkowitz, Palo Alto, Calif.

[73] Assignee: Varian Associates, Inc., Palo Alto, Calif.

[21] Appl. No.: 588,834

[22] Filed: Mar. 12, 1984

Related U.S. Application Data

[62] Division of Ser. No. 107,106, Feb. 26, 1979, Pat. No. 4,375,676, which is a division of Ser. No. 353,263, Mar. 1, 1982, Pat. No. 4,481,608.

[51] Int. Cl.³ .............................................. G01R 33/08
[52] U.S. Cl. ................................ 324/312; 324/307; 364/900
[58] Field of Search ............... 364/900, 200; 324/300, 324/307, 309, 312

[56] References Cited

U.S. PATENT DOCUMENTS

| | | | |
|---|---|---|---|
| 3,293,616 | 12/1966 | Mullery et al. | 340/172.5 |
| 3,593,306 | 7/1971 | Toy | 364/200 |
| 3,792,444 | 2/1974 | Spinner | 340/172.5 |
| 3,873,909 | 3/1975 | Ernst | 324/312 |
| 4,065,714 | 12/1977 | Hill | 324/312 |
| 4,115,730 | 9/1978 | Mansfield | 324/309 |
| 4,176,400 | 11/1979 | Heckel | 364/900 |
| 4,191,919 | 3/1980 | Haney et al. | 324/312 |
| 4,354,157 | 10/1982 | Feiner | 324/312 |
| 4,375,676 | 3/1983 | Berkowitz | 364/900 |
| 4,481,608 | 11/1984 | Berkowitz | 364/900 |

Primary Examiner—Michael J. Tokar
Attorney, Agent, or Firm—Stanley Z. Cole; Edward H. Berkowitz

[57] ABSTRACT

Cyclic instrument control and data acquisition functions which are critically dependent upon synchrony are directed from a computer based system including a FIFO buffer adapted to feedback the most recently active word from its output register and re-store said word at a corresponding sequential position in the FIFO queue. To accommodate complex and interleaved control and data acquisition cycles, each FIFO word has a state portion for commanding external devices, a persistence portion for specifying the duration of selected state active in the FIFO output buffer for a desired persistence interval, and a repetition portion for specifying the number of consecutive discrete repetitions of the currently active state-persistence datum at the output of the FIFO. Termination of the cyclic sequence is accomplished at the expiration of a preselected number of complete cycles. The FIFO input address is selected automatically in accord with the number of words comprising a single complete sequence of instrument control/data acquisition functions.

8 Claims, 4 Drawing Figures

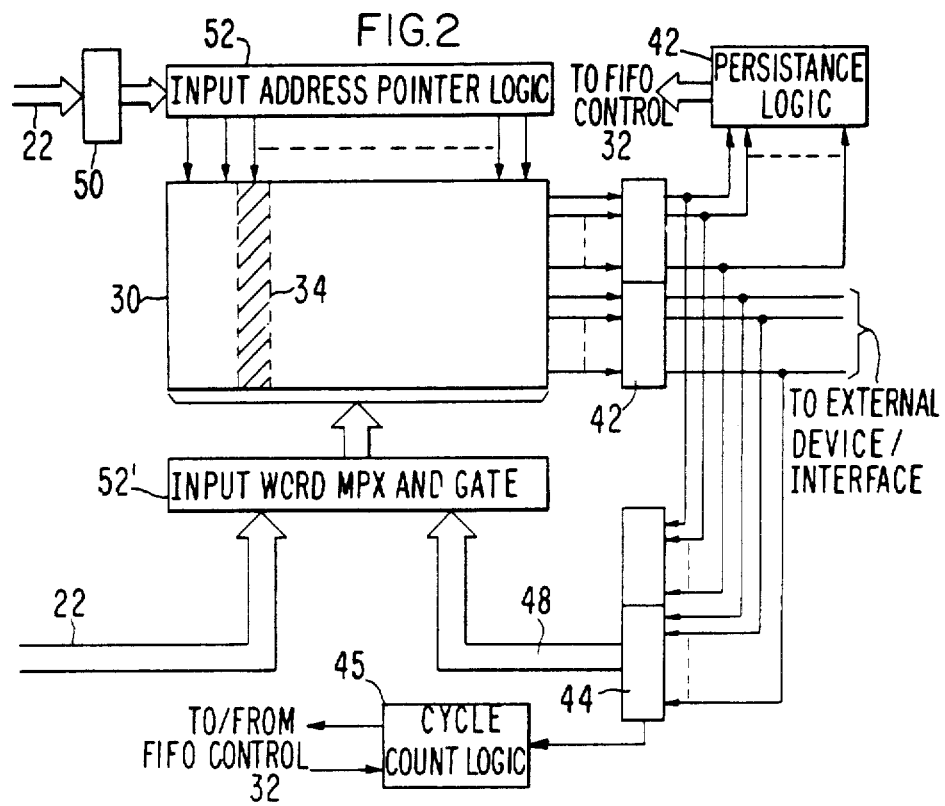
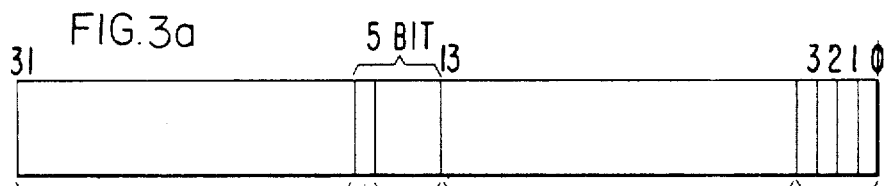
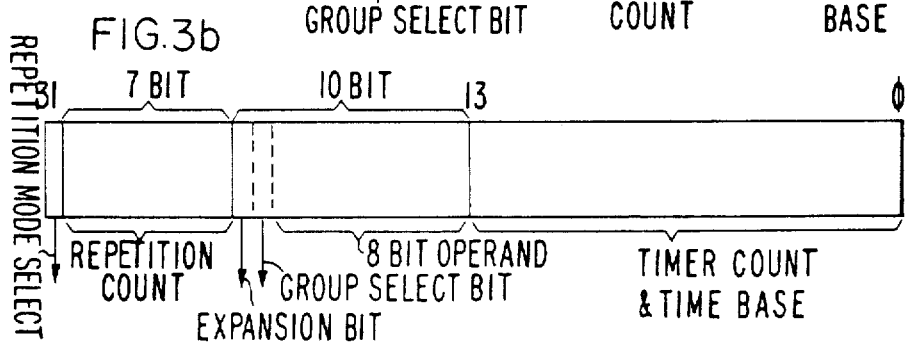

NMR SPECTROMETER INCORPORATING A RE-ENTRANT FIFO

CROSS REFERENCE TO RELATED PATENTS

This invention is a division of U.S. Ser. No. 107,106, filed 2-26-79, now U.S. Pat. No. 4,375,676. Copending U.S. Ser. No. 353,263 filed 3-1-82, now U.S. Pat. No. 4,481,608 is also a division of U.S. Pat. No. 4,375,676.

DESCRIPTION

This invention pertains to instrumentation for cyclic instrument control and data acquisition and particularly to the data acquisition and control aspect of Fourier transform NMR spectroscopy apparatus.

BACKGROUND OF THE INVENTION

FT-NMR spectroscopy is acutely dependent upon modern real time data acquisition methods. A computer based system is dictated by the multiple requirements for control of the spin excitation process, monitoring of system operating parameters, response to operator intervention, acquisition of time domain data, time averaging of such data, Fourier transformation operations on the data and subsequent data reduction. Accordingly, considerable burden is placed upon any single processing unit to accommodate all of these functions while maintaining the necessary data acquisition rate with required synchrony.

The most recent prior art approach to this problem segregates functions in a multiple processor system linked by a common bus and sharing access to a common memory. One of such processors is a special purpose acqustion processor dedicated to commanding the pulse sequence of the spectrometer, monitoring the spectrometer parameters, commanding data conversion by the analog-to-digital converter, hereafter ADC, and performing time averaging operations on the acquired data. The general purpose processor functions as a host, interpreting keyboard commands for general operating purposes and serving to operate upon frequency domain data for desired data reduction, performing Fourier transformation of the time averaged data to the frequency domain, and performing display and output operation. The various functions are accommodated by linked but otherwise independent processors. To assure synchrony in the acquisition of time domain data and to satisfy the various demands upon it, the system is structured upon a priority interrupt organization. This system is especially characterized in the manner in which the acquisition processor, by its structural coupling with the spectrometer, avoids overlap between spectrometer control and data acquisition functions. This is accomplished in part by stacking a series of commands in an advancing sequence buffer. (The advancing sequence buffer comprises a plurality of serially communicating registers for advancing a sequence of digital words toward an output buffer. Thus the advancing sequence buffer is known as a "first in-first out" or FIFO buffer.) Each command word comprises an operation portion and a persistence time portion. The internal FIFO advance signal is then controlled by a timing means which decodes the persistence time portion and maintains the currently active command word at the output register of the FIFO for the specified persistence time. At the termination of the currently active persistence interval, the FIFO content is then advanced. This technique permits the acquisition processor to accommodate certain of its nonsynchronous functions during the autonomous operation of the FIFO. More important, the synchrony of commands to the spectrometer is carefully preserved during the operational discharge of FIFO content. This apparatus is the subject of U.S. Pat. No. 4,191,919, commonly assigned with the present invention.

The above-referenced apparatus preserves synchrony and frees the acquisition processor only for the period jointly defined by the number of command words accommodated by the FIFO and by the respective persistence times of such words. Because the number of transient waveforms may be large, the number of samples defining each waveform also quite large, and the number of excitation and auxiliary commands indefinite, the above-described prior art apparatus requires frequent servicing of the FIFO by the acquisition processor. Consequently, the interrupt rate at the acquisition processor, although reduced (over a conventional priority interrupt organized system), may still be quite high and require substantial penalty in the software for accommodating the various levels of priority required.

Sequence buffers which operate on a first in-first out principle have been known in the computer art for many years for processing serial word strings for input-output operations. Such applications have been addressed to such aspects as matching disparate information processing rates of the digital processor and the communicating peripheral device for strings of arbitrary length.

Shift registers are another class of apparatus in which a number of parallel bits are subject to serial advance or retard. Shift registers are also known in a form wherein the output is fed back to the input of the register to sequentially process the individual bits of a digital word. These structures are employed for parallel to serial transformation, arithmetic operation or single bit string manipulation in the prior art.

SUMMARY OF THE INVENTION

It is an object of the invention to improve the efficiency of a system for concurrent data acquisition and control of instrument parameters of a Fourier transform spectrometer, or like instrument for which the data acquisition requirements are cyclic in nature.

In one feature of the invention, a queue of command words specifying the series of states of the apparatus and the persistence time of such states is transmitted to a FIFO buffer for sequential advancement toward the output register of the FIFO.

In another feature of the invention, each state-specifying command word further includes a portion defining the number of repetitions for consecutive executions of said command and word repetition means are provided to accomplish the repetition of the command word for its specified persistence times.

In still another feature of the invention, at the conclusion of the repetition count, the command which has been most recently executed at the FIFO output is returned to a corresponding position in the queue, whereby an endless loop of commands rotates through said FIFO output register.

In again another feature of the invention, the FIFO is provided with means for selecting the input address of the FIFO for storing a word therein at the physical end of the queue and transfer means are provided for transferring the word currently active at the output of the FIFO to the selected input position whereby a FIFO of given physical word capacity is adapted to accommodate a logical sequence of words fewer in number compared to the maximum FIFO capacity.

In still yet another feature of the invention, means are provided to specify a desired number of rotations of the queue through the FIFO output and termination means act in accordance therewith to conclude the acquisition of data for the currently existing measurement.

In another feature of the invention, the persistence time portion for a particular command state and the state specifying portion for such command state reside in successive FIFO words whereby the initialization of persistence time controlling apparatus may be carried out prior to the gating to the output register of the corresponding command state specifying portion.

BRIEF DESCRIPTION OF THE DRAWINGS

FIG. 2 is a block diagram of one embodiment of the FIFO of the present invention. FIG. 3a shows one choice of FIFO output word format for an NMR system of the present invention.

FIG. 3b shows another choice of FIFO output word format for an NMR data system of the present invention.

DESCRIPTION OF THE PREFERRED EMBODIMENT

Figure 1:
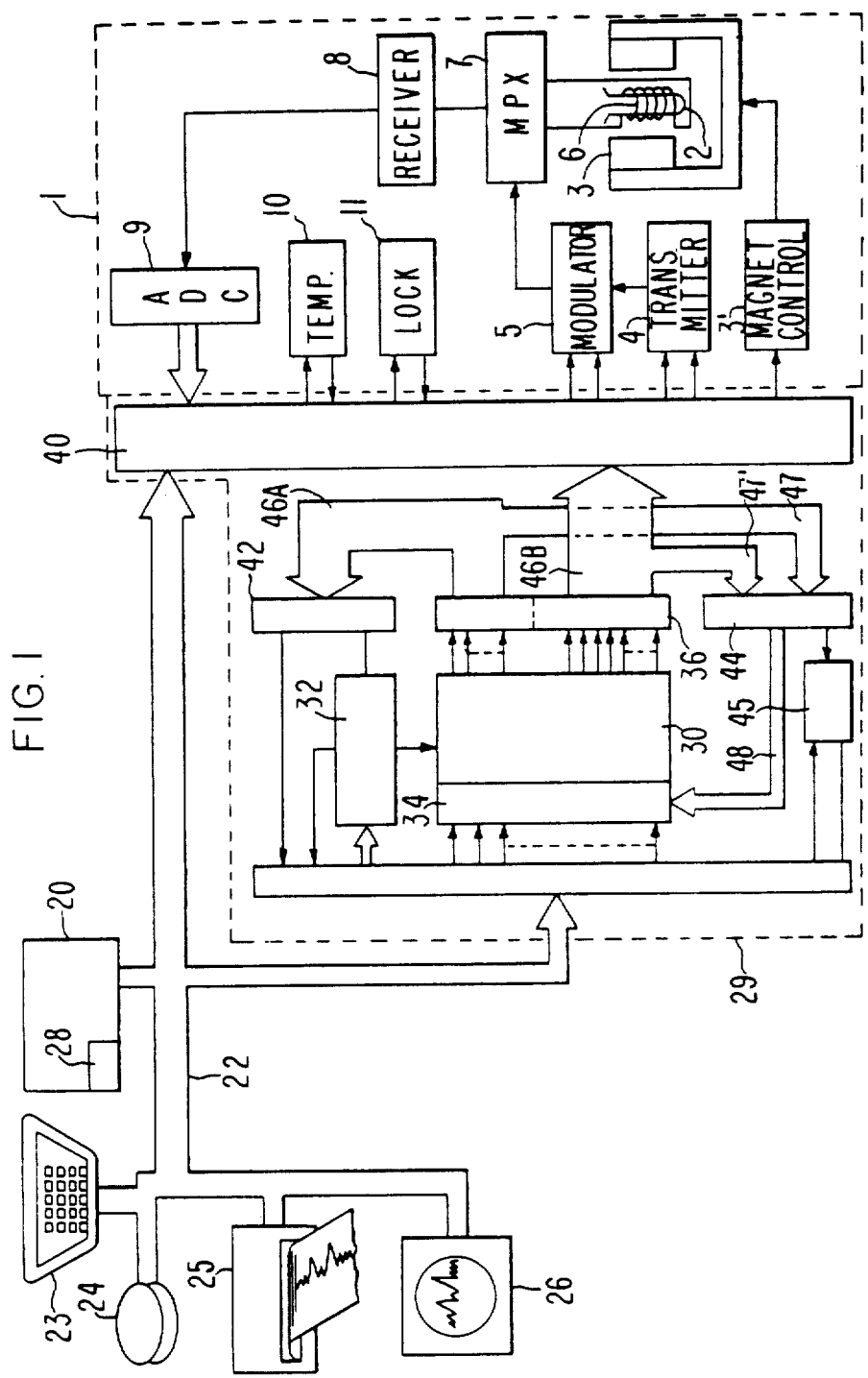
FIG. 1 is a block diagram of a data acquisition system employing the invention.

FIG. 1 exemplifies the present invention applied to the data acquisition and control functions of a modern Fourier transform NMR spectrometer 1. The latter apparatus is broadly and symbolically typified by a sample of matter 2 for analysis subject to a magnetic field provided by magnet 3 and magnet controller 3'. One or more RF transmitters 4 and associated modulators and pulse formers 5 are connected to a probe assembly 6 through a multiplexer 7. A receiver 8, also multiplexed to the probe 6, detects resonant signals induced in the sample 2. Wave forms of the transient resonances are digitized by ADC 9. Instumental variables such as sample temperature, magnetic field-frequency lock conditions and the like are also monitored and may be altered under computer control to maintain desired constant conditions.

A computer or system of processors 20 is also provided to automatically acquire and evaluate incoming information from the spectrometer 1 and as well to issue outgoing signals to maintain desired instrumental conditions and to control the data acquisition sequence. By way of example, this may require responding to temperature and field frequency lock conditions, gating on and off the transmitter and receiver, modulating transmitter signals to realize pulse sequences having desired properties for exciting resonance in the sample, initiating digitization of the resonant signal at precisely defined intervals and strobing the result of such digitization to the processor system 20.

Communication between the processor 20 and its environment comprises input-out (I/O) bus 22. In addition to controlling the data source (spectrometer 1) and reading data generated by the data source, the prototypical data acquisition system must communicate with mass storage, for example disc memory 24 for storage of large data arrays, operating system, library and program requirements. In addition, hard copy output must eventually be generated as symbolized by plotter 25 or like device; visual display 26 allows monitoring of the progress of the experiment during acquisition to correct errors, select operating conditions, or to alter the course of the experiment as appropriate after early inspection of the data. Keyboard 23 is also connected to the I/O bus 22 to provide means to carry out desired alterations of the course of the experiment, to schedule sequences of operations, provide required numerical parameters and the like.

A plurality of separate functions as represented by the above discussion are accommodated by requiring the computer to respond to each function according to some predetermined priority hierarchy. Thus a key stroke on keyboard 23 may generate a low priority signal to which the attention of the computer may be delayed without loss of data for some period because the human intervenor does not generate data through the keyboard at a rate requiring more immediate attention. On the other hand, disc file 24 may require the computer to respond within some tens of microseconds for acceptance of data from the disc file or like mass storage. Response to "data ready for input" conditions from the ADC 9 may demand a response time substantially shorter than the inverse sampling rate which could reach magnitudes of order 10 MHz. Commands to initiate sampling of a wave form U(t) at precise values of time, t, require very high priority to assure availability of the computer to establish control of the variable t within the desired tolerance (of the order of tens of nanoseconds). All of these diverse hierarchical functions are achieved by priority interrupt system 28 responsive to interrupt signal originating in an external device and transmitted over the I/O bus 22. In response to any interrupt of higher priority than the task currently in progress, software operates to store the status of the system and initiate the present higher priority task at the conclusion of which the next lower priority task is resumed. Thus, a considerable number of steps are required at each interrupt. As thus described, this corresponds to a conventionally organized data acquisition system. The present invention is directed to reducing the interrupt rate for a certain class of interrupts and thereby to decouple those tasks from the routine stream of interrupt activity. Thus the burden for interrupt service and the concomitant housekeeping activities required is strongly reduced for computer system 20.

This is accomplished in the present invention by a portion of the control interface 29 as hereinafter described. The central member of this functional block is FIFO buffer 30 and associated control logic 32. The FIFO is a known sequence buffer which has an input register 34 and an output register 36. A sequence of digital words presented to the FIFO 30 are stored in successive locations of the FIFO and FIFO control logic 32 generates command pulses which advance the content of the successive FIFO addresses from input register 34 to output register 36. Such control logic also generates status signals and controls input to the buffer 30.

As in the previously referenced U.S. Ser. No. 907,650, the digital word processed by FIFO 30 comprises a command, or state portion to select the state of spectrometer 1 and a persistence portion which specifies the duration of the selected state. Thus, timer logic 42 receives the persistence portion of the word from data path 46A and initiates a count down in response thereto and at the conclusion of the persistence interval issues a countdown complete signal to FIFO control logic 32. At that point the currently active state is terminated and the content of the FIFO is advanced introducing the next sequential work to output register 36, thus initiating a new state and persistence interval at the output register 36. This register 36 comprises portions 36A and 36B. Reference to output register 36 is directed to the entire register operating as such. As in the prior art, output register 36 communicates via data path 46B directly or through an appropriate interface 40 with spectrometer 1.

In the present invention the datum currently resident in output register 36 is transferred to input register 34 over data path 47, 47', 48 in cooperation with logic sub unit 44. The use of this feature of the invention permits complex sequences of commands to be accommodated within a FIFO of modest maximum capacity. As one of its functions logic sub unit 44 includes counter means for counting the number of times a full sequence of command words rotates through output register 36. This logic unit 44 comprises subportions 44A and 44B for the accommodation of corresponding portions of the content of output register 36. Reference to logic subunit 44 is directed to operational features of the entire logic subunit. Logic 45 processes initialization of the rotation count from bus 22 and provides the necessary status signals to reflect the condition of the system. Where the entire sequence is retained within the FIFO this feature permits repetition of the sequence for a preset number of resonance excitations, terminating the present measurement. Alternative means for terminating the FIFO operation through a halt command is realized by insertion of an appropriately coded control word which is interpreted by timer logic 42 to halt the FIFO and set a status bit to so indicate to the data acquisition logic.

It has been noted above that the sequence length is assumed to be less than the maximum FIFO capacity. It will also be noted that the maximum FIFO capacity is not necessarily a multiple of a particular selected repetitive command sequence. Although the invention is easily understood on such an assumption, the general case requires a variable length sequence of command words to accommodate flexibility of experiments. This can be accomplished with a conventional FIFO structure but a limitation is introduced in the form of the propagation time from the input register of the FIFO to the end-of-queue, or first available address of the FIFO. In view of the above considerations, a variable length FIFO is preferred. A representative such device is symbolically described in FIGS. 1 and 2. The FIFO length is initialized by data received on input 22 which is latched in a portion 50 of FIFO control logic 32 to define a pointer to the FIFO address which is to receive input and to disable FIFO words not comprehended between the output register and the selected input address. FIFO 30 and FIFO control 32 are substantially conventional in organization except that the FIFO is adapted by straightforward gating means (input address pointer logic 52 and input word multiplexer 52') to provide selectable length under control of the processor during the initialization and cyclic operation. During ordinary (cyclic) operation the FIFO control 32 issues a strobe pulse to the FIFO 30 to advance the sequence of words by transferring each word to the next adjacent FIFO address. The strobe pulse is commanded from a countdown timer contained within persistence logic 42. Persistence logic 42 decodes the persistence portion of the command word as it is strobed to output register 36 and initiates a countdown. When the countdown reaches zero, a signal to FIFO control 32 initiates the next FIFO advance strobe pulse. Persistence logic 42 also detects a legal halt (for example, a maximum or a minimum persistence time code) and sets a FIFO halt flag to so inform the processor.

The implementation of a sequence of control words which exceeds the maximum capacity of the FIFO requires partial operation in a non-feedback mode more fully described in above-referenced U.S. Pat. No. 4,191,919. Thus, operation in this partial non-feedback mode does not result in transfer of the content of output register 36 to the FIFO input to maintain the sequence. In this mode, imminent FIFO underflow is indicated by a status bit which initiates an interrupt to the processor 20 for reloading the FIFO 30 with the next required word of the command word sequence. In this mode of operation the control word repetition feature of the present invention is operative to reduce the interrupt rate by maximizing in the FIFO 30 the number of discrete command steps to be realized by the spectrometer 1. A simple example is apparent in the use of the repetition feature of the present invention to completely specify in a single word the entire set of commands to an ADC to initiate data conversion and the precise repetition frequency thereof. (In digitization of a complex waveform for Fourier decomposition, the waveform must be sampled a large number of times at precisely spaced intervals.) The present invention significantly improves the capability of the data acquisition/control structure of above-referenced U.S. Pat. No. 4,191,919 in that non-redundant and cyclic operations may be conveniently joined. For example, it may be desired to repetitively execute a subset of states within a given measurement. The simple repetition of the data conversion operation described above may include in some instances a more complex subset of instructions including data conversion of a single point, such subset to be repeated for the large number of discrete data points necessary to characterize the desired time domain data.

Turning now to FIG. 3a, there is shown one representative choice of format for a 32 bit FIFO output word ultimately directed to output register 36. A persistence interval is specified with a timing count subfield comprising 10 bits and a time base subfield of 4 bits. The time base subfield supplies a power of ten which multiplies the timing count subfield. (The particular word division and bit allocation is illustrative only.) The remaining group of 18 bits are divided between specifying both the state of the apparatus and the number of repetitions. The allocation of bits for state specification is dependent upon the possible number of distinctive substates which are concurrently compatible. Ordinarily, an FT-NMR system is susceptible to a very few concurrently specified substates which this basis, easily divided into two independent command groups along the lines of Table 1 (the commands of Table 1 are illustrative only and a detailed explanaton thereof is not essential to understanding the present invention. A 5 bit subfield is sufficient to specify any one of the desired operands. FIG. 3a illustrates such a choice wherein one bit of a 5 bit operand sub-field is available to designate either of two such command groups. The remaining 4 bits can specify up to 16 combinations of the 8 substates available in either group. Thus, a limited degree of microprogrammability is available while a substantial area for non-compatible substate superpositions (errors) is eliminated. In the prior art a 16-bit subfield was allocated to the specification of output commands. In such case the functions were allocated on a dedicated bit-per state basis permitting the concurrent specification of up to 16 substates from the 16-bit field where in fact nearly all of the $2^{16}-1$ possible composite states would be meaningless. For a general apparatus such a large field is, of course, appropriate, although it is not optimum where a substantial portion of mathematically possible combinations, here $2^{16}-1$, are not physically compatible.

| Command Group Bit = 0 | Command Group Bit = 1 |
| --- | --- |
| OBSERV XMTR ON | OBSERVE RCVR |
| DECOUPLER ON | ADC CONVERSION START |
| RF 90° | ADC MODE 1 |
| RF 180° | ADC MODE 2 |
| MODULATION MODE A | OBSERVE/LOCK |
| MODULATION MODE B | QUADRATURE/ NO QUADRATURE |
| HOMOSPOILING | DECOUPLER 90° |
| DECOUPLER HIGH/LOW | DECOUPLER 180° |

An intermediate choice is shown in FIG. 3(b) where a 10-bit operand field is shown. In such case, and assuming a multiple command group division similar to Table i, there is available a bit-for-function allocation for each of the 8 substates, a group designation bit and an extra bit which could be used to expand the number of groups or the number of functions. In this format a selected operand may well be included in more than one group of operands.

These format choices for the command, or state portion of the word determine the field available for the repetition count field. For the short command field of FIG. 3(e), a larger repetition field is available. Thus, a 13-bit repetition field permits specifying that the current state be repeated up to $2^{13}-1$ times in addition to the initial statement of the operand. A repetition of zero implies that the currently stated operand is not repeated at the end of the corresponding persistence interval, and the FIFO content is than advanced to deliver the next sequential word to the output register. These long repetition count situations are useful for specifying a corresponding number of successive identical state commands, e.g., conversion commands to the ADC for sampling a time-dependent wave form at precisely delineated intervals, as specified by the persistence interval. It should be noted that for ADC command purposes a pulse is ordinarily delivered to command the ADC as, 5 for example, to reset the ADC, to initiate the conversion and the like, while the persistence interval in that circumstance may be interpreted by the apparatus as an interval between pulses.

For the longer command field of FIG. 3(b) the repetition count field is abbreviated in length requiring a logarithmic-linear interpretation. A repetition mode select bit designates whether the 6-bit repetition field, $n=0, 1 \ldots 2^n-1$ specifies 0 to 63 repetitions, or on the other hand, the selection bit may designate that n is interpreted as $2^{k-m}$ for long repetition counts, where k is some convenient maximum exponent and m is the desired number of bits (k>m).

The several portions or subfields described above do not necessarily reside in the same word. For example, the timing subfield may reside in the next adjacent word with respect to the output register.

Another embodiment of the FIFO based systems described above lacks a persistence time decoding structure but realizes the persistence selection result from a repetition function. The repetition field is in effect the time counter and the time base is supplied by the processor clock available over bus 22, or preferably a faster internal FIFO clock. The treatment of the control word as either discrete repetitions or as a state continuously persisting for an interval of n time units is selected in accord with a prescribed bit of the command word and implemented within the interface 40.

In one embodiment initialization may take the form of initializing one of dual countdown registers, the remaining one being currently active. At the conclusion of the currently active countdown, the countdown=0 and repetitiion bit in the active state will gate the second countdown on the first countdown off. Where no repetition bit is encountered, the sequence is advanced in straightforward fashion at the termination of the currently active state.

Another embodiment for achieving persistance selection from repetition is realized in a more general type of sequence buffer wherein bidirectional internal transfer means are provided for either advancing the FIFO content toward the output register 36 or alternatively, teransferring the content in the opposite direction by at least one address increment prior to advancing the sequence again toward the output register. In this form, repetition is realized in conjunction with a latched output register 36 wherein output register 36 is loaded, the repeat command is decoded (as by a logic unit analogous to unit 42) and the reverse transfer accomplished while the output buffer content is maintained. In this realization, the repetition count field initializes a countdown circuit which maintains the prescribed state in output register 36A until the countdown is complete. At that point, the next strobe pulse advanaces the sequence of control words transferring the next output word to the output register. Because the word now transferred to output register 36 is the same word previously shifted into output register 36 then returned to the last FIFO address, a countdown flag set by the countdown circuit causes a double transfer forward. Thus, the repeated command is transferred to the feedback path to input buffer 34 for maintaining the sequence.

Although an NMR spectrometer has been selected as the illustrative example for the present invention it will be obvious that any data acquisition system which must issue periodic commands and accept aperiodic interrupts may use the present invention profitably. It will be apparent that many changes could be made in the above method and apparatus and many apparently different embodiments of this invention could be made without departing from the scope thereof; it is therefore intended that all matter contained in the above description and shown in accompanying drawings shall be interpreted as illustrative and not in a limiting sense.

I claim:

1. In an NMR spectrometer utilizing a stored program digital processor for execution of a desired sequence of operations, a first class of said operations directed to controlling the status of said spectrometer and another class of said operations directed to acquiring data from said spectrometer, a digital sequence buffer apparatus including an input register and an output register and a plurality of intermediate registers for retaining a plurality of digital words, each said word comprising an operand portion for specifying the instantaneous configuration of said spectrometer and a persistence portion for specifying the persistence interval of each operand, and a repetition portion for specifying the desired number of sequential repetitions of the currently active word, first means responsive to the persistence portion of said digital word for sustaining the currently active operand for the desired persistence interval, second means responsive to the repetition portion for re-initiating the currently active operand at the completion of the persistence interval thereof, said second means operative to continue said repetitions until the operand has been repeated for the desired number of repetitions, third means for advancing the content of said buffer toward said output register of said buffer apparatus when the persistence portion of the currently active word has been completed for the number of sequential repetitions specified by said repetition portion, and means for re-introducing said sequence of instruction words to the input portion of said sequence buffer whereby said sequence is preserved.

2. In an NMR spectrometer utilizing a stored program digital processor for execution of a desired sequence of operations, a first class of said operations directed to controlling the status of said spectrometer and another class of said operations directed to acquiring data from said spectrometer, a digital sequence buffer apparatus including an input register and an output register and a plurality of intermediate registers for retaining a plurality of digital words, each said word comprising an operand portion for specifying the instantaneous configuration of said spectrometer and a persistence portion for specifying the persistence interval of each operand, first means responsive to the persistence portion of said digital word for sustaining the currently active operand for the desired persistence interval, second means responsive to the repetition portion for re-initiating the currently active operand at the completion of the persistence interval thereof, said second means operative to continue said repetitions until the operand has been repeated for the desired number of repetitions, third means for advancing the content of said buffer toward said output register of said buffer apparatus when the persistence portion of the currently active word has been completed, and means for re-introducing said sequence of instruction words to the input portion of said sequence buffer whereby said sequence is preserved.

3. The NMR spectrometer of claim 2 comprising cycle counter means for counting the number of times said complete sequence has been re-introduced to the input portion of said sequence buffer.

4. The NMR spectrometer of claim 3 comprising means responsive to said counter means for causing said FIFO to halt after a pre-determined number of re-introductions of said complete sequence.

5. The method of operating an NMR apparatus to control same and to acquire data therefrom, comprising
defining a complete sequence of descriptors of operational states of said apparatus required to cause excitation and detection of gyromagnetic resonance conditions according to a pre-selected operational procedure, prescribing for each state of said apparatus, a corresponding persistance interval for each state to be maintained, establishing each state and maintaining said state for its corresponding persistence interval, re-introducing said descriptor of each said state and the corresponding persistence parameter in said sequence whereby said complete sequence is preserved for repetition of execution of said complete sequence, repeating said step of establishing, maintaining and re-introducing.

6. The method of operating an NMR spectrometer according to claim 5 wherein said step of prescribing comprises prescribing for each state a repetition count for causing said state persisting for said corresponding persistence interval to repeat the number of repetitions specified by said repetition count.

7. The method of claim 5 or 6 comprising counting the number of times said complete sequence is re-introduced for repetition.

8. The method of claim 7 comprising terminating said step of repeating when said number of times meets a pre-selected criteria.

* * * * *